United States Patent [19]

Yale et al.

[11] 4,022,790
[45] May 10, 1977

[54] HYDROGENATED DIELS-ALDER ADDUCTS OF BENZDIAZEPINES

[75] Inventors: Harry L. Yale, New Brunswick; James A. Bristol, Boonton, both of N.J.

[73] Assignee: E. R. Squibb & Sons, Inc., Princeton, N.J.

[22] Filed: July 20, 1976

[21] Appl. No.: 707,135

Related U.S. Application Data

[62] Division of Ser. No. 568,358, April 15, 1975, Pat. No. 3,984,418.

[52] U.S. Cl. .......................... 260/293.55; 424/267
[51] Int. Cl.[2] ...................................... C07D 471/04
[58] Field of Search ............................ 260/293.55

[56] References Cited

UNITED STATES PATENTS

| | | | |
|---|---|---|---|
| 3,639,408 | 2/1972 | Nagata et al. | 260/293.53 |
| 3,763,183 | 10/1973 | Carabateas | 260/293.3 |
| 3,868,372 | 2/1975 | Hardtmann | 260/251 |

*Primary Examiner*—Cecilia M. S. Jaisle

*Attorney, Agent, or Firm*—Lawrence S. Levinson; Merle J. Smith; Donald J. Barrack

[57] ABSTRACT

Compounds having the structure

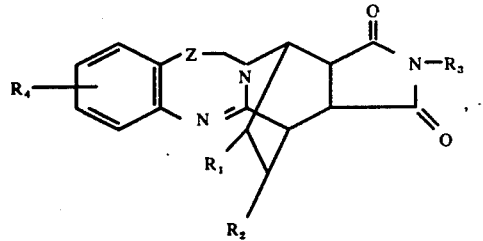

and the pharmaceutically acceptable salts thereof; wherein Z is oxygen, sulfur or methylene; $R_1$ is hydrogen, halogen, alkyl, aryl or arylalkyl; $R_2$ is hydrogen, alkyl, aryl, or arylalkyl; $R_3$ is hydrogen, alkyl, aryl or arylalkyl; and $R_4$ is hydrogen, halogen, alkyl, phenyl, dialkylamidosulfonyl or trifluoromethyl; have useful central nervous system activity.

10 Claims, No Drawings

HYDROGENATED DIELS-ALDER ADDUCTS OF BENZDIAZEPINES

This is a division of application Ser. No. 568,358, filed Apr. 15, 1975, now U.s. Pat. No. 3,984,418, patented Oct. 5, 1976.

SUMMARY OF THE INVENTION

Compounds having the structure

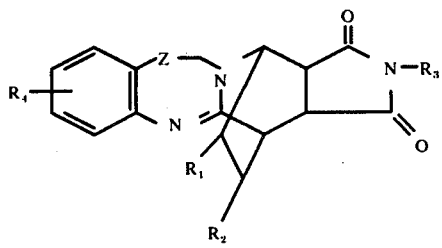

and the pharmaceutically acceptable salts thereof, have useful pharmacological activity. In formula I, and throughout the specification, the symbols are as defined below:

Z is oxygen, sulfur or methylene;
$R_1$ is hydrogen, halogen, alkyl, aryl or arylalkyl;
$R_2$ is hydrogen, alkyl, aryl or arylalkyl;
$R_3$ is hydrogen, alkyl, aryl or arylalkyl; and
$R_4$ is hydrogen, halogen, alkyl, phenyl, dialkylamidosulfonyl or trifluoromethyl;

with the proviso that when Z is oxygen or sulfur, and $R_4$ is phenyl or dialkylamidosulfonyl, $R_4$ must be para to the oxygen or sulfur atom.

The term "alkyl", as used throughout the specification, refers to straight or branched chain alkyl groups having 1 to 4 carbon atoms. Methyl is the preferred alkyl group.

The term "aryl", as used throughout the specification, refers to phenyl or phenyl substituted with halogen, alkyl or alkoxy. Phenyl is the preferred aryl group.

The term "halogen", as used throughout the specification, refers to chlorine, fluorine and bromine. Chlorine and bromine are the preferred halogens.

The term "alkoxy", as used throughout the specification, refers to groups having the formula Y—O— wherein Y is alkyl as defined above. Methoxy is the preferred alkoxy group.

DETAILED DESCRIPTION OF THE INVENTION

The compounds of this invention have useful central nervous system stimulant activity in mammalian species, such as rats, dogs, etc., and can be used in the same manner as dextroamphetamine for the treatment of drowsiness or for the supression of appetite, or in the same manner as imipramine for the treatment of depression.

The compounds of this invention can be administered in a daily dose of from about 10 milligrams/70 kilograms to 2 grams/70 kilograms, preferably from about 25 milligrams/70 kilograms to 1 gram/70 kilograms. The compounds can be administered orally or parenterally in the form of tablets, capsules elixirs, injectables or the like by incorporating the appropriate dosage of the compound with carriers according to accepted pharmaceutical practice.

The compounds of formula I can be prepared by selectively hydrogenating the double bond in the 14,15-position of compounds having the formula:

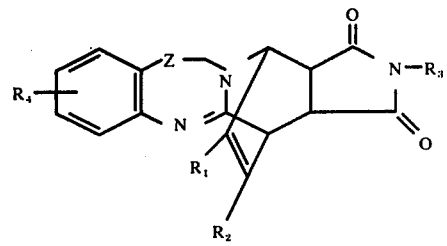

The selective hydrogenation can be carried out using gaseous hydrogen and Raney nickel as the catalyst. Reaction conditions are not critical but the hydrogenation will preferably be run at room temperature at a pressure of about 50 psig.

The compounds of formula II are set forth in U.S. patent application Ser. No. 531,512 filed Dec. 11, 1974. As disclosed therein, the compounds of formula II can be prepared from maleimides having the structure

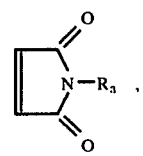

and from tricyclic compounds having the structure

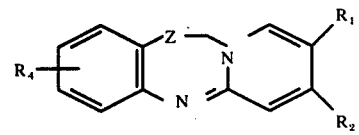

The N-maleimides of formula III are well known in the art and are readily obtainable by reaction of maleic anhydride and an amine having the formula $R_3$—$NH_2$. The compounds of formula IV are known: see, U.S. Pat. No. 3,825,549, issued July 23, 1974; U.S. patent application, Ser. No. 347,938, filed Apr. 4, 1973, now U.s. Pat. No. 3,857,850, issued Dec. 31, 1974; and U.S. application, Ser. No. 347,939, filed Apr. 4, 1973, now U.S. Pat. No. 3,856,801, issued Dec. 24, 1974.

The reaction of a tricyclic compound of formula IV with an N-substituted maleimide of formula III can be carried out in an organic solvent at elevated temperatures. While the choice of solvent and reaction conditions is not critical, the reaction will most preferably be run in an aromatic hydrocarbon solvent, such as xylene, under reflux conditions.

The compounds of formula I can be converted into pharmaceutically acceptable acid addition salts using procedures well known in the art. Illustrative acid addition salts are hydrohalides, especially the hydrochloride and hydrobromide which are preferred, sulfate, nitrate, phosphate, tartrate, maleate, fumarate, citrate, succinate, methanesulfonate, toluenesulfonate, benzenesulfonate and the like.

The compounds of formula I wherein $R_1$ and $R_2$ are hydrogen are preferred.

The compounds of formula I wherein $R_1$, $R_2$ and $R_4$ are hydrogen are preferred.

The following examples are specific embodiments of this invention.

EXAMPLE 1

3a,4,13,13a-Tetrahydro-2-methyl-4,13-ethano1H,6H-pyrrolo[3',4':4,5]pyrido[1,2-c][1,3,5]benzoxadiazepine-1,3(2H)-dione A mixture of 1.54g of 3a,4,13,13a-tetrahydro-2-methyl-4,13-etheno-1H,6H-pyrrolo[3',4':4,5-]pyrido[1,2-c][1,3,5]benzoxadiazepine-1,3(2H)-dione in 150 ml of methanol is hydrogenated in a Parr vessel, using pyrophoric Raney nickel as a catalyst, until 0.005 mole of hydrogen is taken up. The mixture is filtered and the filtrate is concentrated in vacuo to give a solid. This is recrystallized from 40 ml of toluene to give 1.11g of the title compound, melting point 222°–224° C.

EXAMPLE 2

3a,4,10,11,13,13a-Hexahydro-2-methyl-4,13-ethano-1H-pyrrolo[3',4':4,5]pyrido[2,1-b][1,3]benzodiazepine-1,3(2H)-dione, hydrochloride (1:1)

A solution of 1.53g of 3a,4,10,11,13,13a-hexahydro-2-methyl-4,13-ethano-1H-pyrrolo[3', 4':4,5-]pyrido[2,1-b][1,3]benzodiazepine-1,3(2H)-dione in 100 ml of methanol is hydrogenated in a Parr vessel, using pyrophoric Raney nickel as a catalyst, until 0.005 mole of hydrogen is taken up. The mixture is filtered and concentrated to give a solid, which is dissolved in 20 ml of warm isopropanol. This solution is treated with an excess of a solution of hydrogen chloride in isopropanol, and the product that separates is recrystalized from 500 ml of isopropanol to yield 1.18g of the title compound, sintering at 320° C, melting point 344°–347° C.

EXAMPLES 3–29

Following the procedure of Example 1, but substituting the compound listed in column I for 3a,4,13,13a-tetrahydro-2-methyl-4,13-etheno-1H,6H-pyrrolo[3',-4':4,5]pyrido[1,2-c][1,3,5]benzoxadiazepine-1,3-dione, the compound listed in column II is obtained.

| Example | Column I | Column II |
|---|---|---|
| 3 | 3a,4,13,13a-tetrahydro-2-methyl-4,13-etheno-1H,6H-pyrrolo[3',4':4,5]pyrido[1,2-c][1,3,5]-benzothiadiazepine-1,3(2H)-dione | 3a,4,13,13a-tetrahydro-2-methyl-4,13-ethano-1H,6H-pyrrolo[3',4':4,5]pyrido[1,2-c][1,3,5]-benzothiadiazepine-1,3(2H)-dione |
| 4 | 10-chloro-3a,4,13,13a-tetrahydro-2-methyl-4,13-etheno-1H,6H-pyrrolo[3',4':4,5]pyrido-[1,2-c][1,3,5]benzoxadiazepine-1,3(2H)-dione | 10-chloro-3a,4,13,13a-tetrahydro-2-methyl-4,13-ethano-1H,6H-pyrrolo[3',4':4,5]pyrido-[1,2-c][1,3,5]benzoxadiazepine-1,3(2H)-dione |
| 5 | 3a,4,13,13a-tetrahydro-2-phenyl-4,13-etheno-1H,6H-pyrrolo[3',4':4,5]pyrido[1,2-c][1,3,5]-benzoxadiazepine-1,3(2H)-dione | 3a,4,13,13a-tetrahydro-2-phenyl-4,13-ethano-1H,6H-pyrrolo[3',4':4,5]pyrido[1,2-c][1,3,5]-benzoxadiazepine-1,3(2H)-dione |
| 6 | 3a,4,13,13a-tetrahydro-4,13-etheno-15-ethyl-8-trifluoromethyl-1H,6H-pyrrolo[3',4':4,5]-pyrido[1,2-c][1,3,5]benzothiadiazepine-1,3-(2H)-dione | 3a,4,13,13a-tetrahydro-4,13-ethano-15-ethyl-8-trifluoromethyl-1H,6H-pyrrolo[3',4':4,5]-pyrido[1,2-c][1,3,5]benzothiadiazepine-1,3-(2H)-dione |
| 7 | 9-t-butyl-14-chloro-2-(2-phenylethyl)-3a,4,13,-13a-tetrahydro-4,13-etheno-1H,6H-pyrrolo-[3',4':4,5]pyrido[1,2-c][1,3,5]benzothiadiazepine-1,3(2H)-dione | 9-t-butyl-14-chloro-2-(2-phenylethyl)-3a,4,13,-13a-tetrahydro-4,13-ethano-1H,6H-pyrrolo-[3',4':4,5]pyrido[1,2-c][1,3,5]benzothiadiazepine-1,3(2H)-dione |
| 8 | 11-methyl-2-n-propyl-3a,4,13,13a-tetrahydro-4,13-etheno-1H,6H-pyrrolo[3',4':4,5]pyrido-[1,2-c][1,3,5]benzothiadiazepine-1,3(2H)-dione | 11-methyl-2-n-propyl-da,4,13,13a-tetrahydro-4,13-ethano-1H,6H-pyrrolo[3',4':4,5]pyrido-[1,2-c][1,3,5]benzothiadiazepine-1,3(2H)-dione |
| 9 | 2-(4-chlorophenyl)-:-(dimethylamidosulfonyl)-14-(phenylmethyl)-3a,4,13,13a-tetrahydro-4,13-etheno-1H,6H-pyrrolo[3',4':4,5]pyrido[1,2-c]-[1,3,5]benzothiadiazepine-1,3(2H)-dione | 2-(4-chlorophenyl)-9-(dimethylamidosulfonyl)-14-(phenylmethyl)-3a,4,13,13a-tetrahydro-4,13-ethano-1H,6H-pyrrolo[3',4':4,5]pyrido]pyrido[1,2,-c]-[1,3,5]benzothiadiazepine-1,3(2H)-dione |
| 10 | 9-chloro-14-ethyl-2-(3-methylphenyl)-3a,4,13,-13a-tetrahydro-4,13-etheno-1H,6H-pyrrolo[3',4':-4,5]pyrido[1,2-c][1,3,5]benzothiadiazepine-1,3-(2H)-dione | 9-chloro-14-ethyl-2-(3-methylphenyl)-da,4,13,-13a-tetrahydro-4,13-ethano-1H,6H-pyrrolo[3',4':-4,5]pyrido[1,2-c][1,3,5]benzothiadiazepine-1,3-(2H)-dione |
| 11 | 15-n-butyl-10-ethyl-2-isopropyl-3a,4,13,13a-tetrahydro-4,13-etheno-1H,6H-pyrrolo[3',4':-4,5]pyrido[1,2-c][1,3,5]benzothiadiazepine-1,3-(2H)-dione | 15-n-butyl-10-ethyl-2-isopropyl-3a,4,13,13a-tetrahydro-4,13-ethano-1H,6H-pyrrolo[3',4':-4,5]pyrido[1,2-c][1,3,5]benzothiadiazepine-1,3-(2H)-dione |
| 12 | 2-(3-t-butylphenyl)-9,14-diphenyl-3a,4,13,13a-tetrahydro-4,13-ethenol-1H,6H-pyrrolo[3',4':-4,5]pyrido[1,3,5]benzothiadiazepine-1,3(2H)-dione | 2-(3-t-butylphenyl)-9,14-diphenyl-da,4,13,13a-tetrahydro-4,13-ethano-1H,6H-pyrrolo[3',4':-4,5]pyrido[1,2-c][1,3,5]benzothiadiazepine-1,3(2H)-dione |
| 13 | 2-(2-bromophenyl)-14-phenyl-3a,4,13,13a-tetrahydro-4,13-etheno-1H,6H-pyrrolo(3',4':4,5]-pyrido[1,2-c][1,3,5]benzothiadiazepine-1,3-(2H)-dione | 2-(2-bromophenyl)-15-phenyl-3a,4,13,13a-tetra-,4':4,5]-pyrido[1,2-c][1,3,5]benzothiadiazepine-1,3-(2H)-dione |
| 14 | 8,15-dichloro-2-phenyl-3a,4,10,11,13,13a-hexahydro-4,13-etheno-1H-pyrrolo[3',4':4,5]pyrido-[2,1-b][1,3]benzodiazepine-1,3(2H)-dione | 8,15-dichloro-2-phenyl-3a,4,10,11,13,13a-hexahydro-4,13-ethao-1H-pyrrolo[3',4':4,5]pyrido-[2,1-b][1,3]benzodiazepine-1,3(2H)-dione |
| 15 | 2,8,14-trimethyl-3a,4,10,11,13,13a-hexahydro-4,13-etheno-1H-pyrrolo[3',4':4,5]pyrido[2,-1-b][1,3]benzodiazepine-1,3(2H)-dione | 2,8,14-trimethyl-3a,4,10,11,13,13a-hexahydro-4,13-ethano-1H-pyrrolo[3',4':4,5]pyrido 8 2-1-b][1,3]benzodiazepine-1,3(2H)-dione |
| 16 | 15-bromo-8-ethyl-2-(phenylmethyl)-3a,4,10,-11,13,13a-hexahydro-4,13-etheno-1H-pyrrolo-[3',4':4,5]pyrido[2,1-b][1,3]benzodiazepine-1,3(2H)-dione | 15-bromo-8-ethyl-2-(phenylmethyl)-3a,4,10,-11,13,13a-hexahydro-4,13-ethao-1H-pyrrolo-[3',4':4,5]pyrido[2,1-b][1,3]benzodiazepine-1,3(2H)-dione |
| 17 | 2-ethyl-14-phenylmethyl-3a,4,10,11,13,13a-hexahydro-4,13-etheno-1H-pyrrolo[3',4':4,5]-pyrido8 2,1-b][1,3]benzodiazepine-1,3-(2H)-dione | 2-ethyl-14-phenylmethyl-3a,4,10,11,13,13a-hexahydro-4,13-ethao-1H-pyrrolo[3',4':4,5]-pyrido[2,1-b][1,3]benzodiazepine-1,3-(2H)-dione |
| 18 | 2-isopropyl-7:(diethylamidosulfonyl-14- | 2-isopropyl-7-(diethylamidosulfonly-14- |

-continued

| Example | Column I | Column II |
|---|---|---|
| | phenyl-3a,4,10,11,13,13a-hexahydro-4,13-etheno-1H-pyrrolo[3',4':4,5]pyrido[2,1-b]-[1,3]benzodiazepine-1,3(2H)-dione | phenyl-3a,4,10,11,13,13a-hexahydro-4,13-ethano-1H-pyrrolo[3',4':4,5]pyrido[2,1-b]-[1,3]benzodiazepine-1,3(2H)-dione |
| 19 | 2-n-propyl-8-trifluoromethyl-3a,4,10,11,13,-13a-hexahydro-4,13-etheno-1H-pyrrolo[3',4':-4,5]pyrido[2,1-b ][1,3]benzodizepine-1,3-(2H)-dione | 2-n-propyl-8-trifluoromethyl-3a,4,10,11,13,-13a-hexahydro-4,13-ethano-1H-pyrrolo[3',4':-4,5]pyrido[2,1-][1,3]benzodiazepine-1,3-(2H)-dione |
| 20 | 2,6-diphenyl-3a,4,10,11,13,13a-hexahydro-4,13-etheno-1H-pyrrolo[3',4':4,5]pyrido-[2,1-b][1,3]benzodiazepine-1,3(2H)-dione | 2,6-diphenyl-3a,4,10,11,13,13a-hexahydro-4,13-ethao-1H-pyrrolo[3',4':4,5]pyrido-[2,1-b][1,3]benzodiazepine-13,(2H)-dione |
| 21 | 9-bromo-15-methyl-2-phenyl-3a,4,13,13a-tetrahydro-4,13-etheno-1H,6H-pyrrolo-[3',4':4,5]pyrido[1,2-c][1,3,5]benzoxadiazepine-1,3(2H)-dione | 9-bromo-15-methyl-2-phenyl-3a,4,13,13a-tetrahydro-4,13-ethano-1H,6H-pyrrolo-[3',4':4,5]pyrido[1,2-c][1,3,5]benzoxadiazepine-1,3(2H)-dione |
| 22 | 11-bromo-2,14-dimethyl-3a,4,13,13a-tetrahydro-4,13-etheno-1H,6H-pyrrolo[3',4':4,5]-pyrido[1,2-c][1,3,5]benzoxadiazepine-1,3-(2H)-dione | 11-brono-2,14-dimethyl-3a,4,13,13a-tetrahydro-4,13-ethano-1H,6H-pyrrolo[3',4':4,5]-pyrido[1,2-c][1,3,5]benzoxadiazepine-1,3-(2H)-dione |
| 23 | 8-chloro-2-(phenylmethyl)-3a,4,13,13a-tetrahydro-4,13-etheno-1H,6H-pyrrolo[3',4':4,5]-pyrido[1,2-c][1,3,5]benzoxadiazepine-1,3-(2H)-dione | 8-chloro-2-(phenylmethyl)-3a,4,13,13a-tetrahydro-4,13-ethano-1H,6H-pyrrolo[3',4':4,5]-pyrido[1,2-c][1,3,5]benzoxadiazepine-1,3-(2H)-dione |
| 24 | 2-n-butyl-9-isobutyl-14-chloro-3a,4,13,13a-tetrahydro-4,13-etheno-1H,6H-pyrrolo[3',4':-4,5]pyrido[1,2-c][1,3,5]benzoxadiazepine-1,3(2H)-dione | 2-n-butyl-9-isobutyl-14-chloro-3a,4,13,13a-tetrahydro-4,13-ethano-1H,6H-pyrrolo[3',4':-4,5]pyrido[1,2-c][1,3,5]benzoxadiasepine-1,3(2H)-dione |
| 25 | 2-isopropyl-14-methyl-9-phenyl-3a,4,13,13a-tetrahydro-4,13-etheno-1H,6H-pyrrolo[3',4':-4,5]pyrido[1,2-c][1,3,5]benzoxadiazepine-1,3(2H)-dione | 2-isopropyl-14-methyl-9-phenyl-3a,4,13,13a-tetrahydro-4,13-ethao-1H,6H-pyrrolo[3',4':-4,5]pyrido[1,2-c][1,3,5]benzoxadiazepne-1,3(2H)-dione |
| 26 | 2,15-dimethyl-9-trifluoromethyl-3a,4,13,13a-tetrahydro-4,13-etheno-1H,6H-pyrrolo[3',4':-4,5]pyrido[1,2-c][1,3,5]benzoxadiazepine-1,-3(2H)-dione | 2,15-dimethyl-9-trifluoromethyl-3a,4,13,13a-tetrahydro-4,13-ethano-1H,6H-pyrrolo[3',4':-4,5]pyrido[1,2-c][1,3,5]benzoxadiazepine-1,-3(2H)-dione |
| 27 | 9,14-diphenyl-2-(phenylmethyl)-3a,4,13,13a-tetrahydro-4,13-etheno-1H,6H-pyrrolo[3',4':-4,5]pyrido[1,2-c][1,3,5]benzoxadiazepine-1,3(2H)-dione | 9,14-diphenyl-2-(phenylmethyl)-3a,4,13,13a-tetrahydro-4,13-ethazo-1H,6H-pyrrolo[3',4':-4,5]pyrido 8 1,2-c][1,3,5]benzoxadiazepine-1,3(2H)-dione |
| 28 | 9-(dimethylamidosulfonyl)-15-(phenylmethyl)-3a,4,13,13a-tetrahydro-4,13-etheno-1H,6H-pyrrolo[3',4':4,5]pyrido[1,2-c][1,3,5]benzodiazepine-1,3(2H)-dione | 9-(dimethylamidosulfonyl)-15-(phenylmethyl)-3a,4,13,13a-tetrahydro-4,13-ethano-1H,6H-pyrrolo[3',4':4,5]pyrido[1,2-c][1,3,5]benzodiazepine-1,3(2H)-dione |
| 29 | 2-isobutyl-3a,4,13,13a-tetrahydro4,13,-etheno-1H,6H-pyrrolo[3',4':4,5]pyrido[1,2-c][1,3,5]-benzoxaidazepine1,3(2H)-dione | 2-isobutyl-3a,4,13,13a-tetrahydro-4,13-ethano-1H,6H-pyrrolo[3',4':4,5]pyrido[1,2-c][1,3,5]-benzoxadiazepine-1,3(2H)-dione |

What is claimed is:

1. A compound having the structure

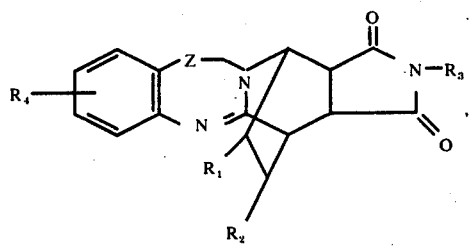

or a pharmaceutically acceptable salt thereof, wherein Z is oxygen or sulfur; $R_1$ is hydrogen, halogen, alkyl, aryl or arylalkyl; $R_2$ is hydrogen, alkyl, aryl or arylalkyl; $R_3$ is hydrogen, alkyl, aryl or arylalkyl; and $R_4$ is hydrogen, halogen, alkyl, phenyl, dialkylamidosulfonyl or trifluoromethyl; with the proviso that when $R_4$ is phenyl or dialkylamidosulfonyl, $R_4$ must be para to the oxygen or sulfur atom; wherein aryl is phenyl or phenyl substituted with halogen, alkyl or alkoxy; and alkyl and alkoxy are groups having 1 to 4 carbon atoms.

2. A compound in accordance with claim 1 having the structure

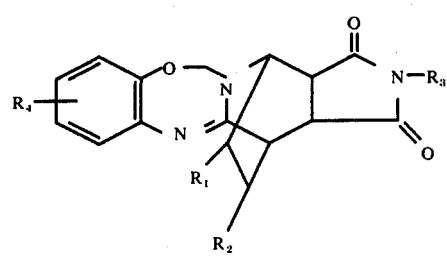

3. A compound in accordance with claim 1 having the structure

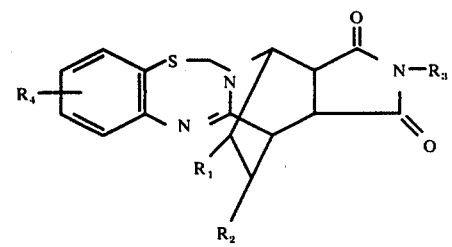

4. A compound in accordance with claim 1 wherein $R_1$ and $R_2$ are hydrogen.

5. A compound in accordance with claim 1 wherein $R_3$ is hydrogen.

6. A compound in accordance with claim 1 wherein $R_3$ is alkyl.

7. A compound in accordance with claim 1 wherein $R_3$ is aryl.

8. A compound in accordance with claim 1 wherein $R_3$ is arylalkyl.

9. A compound in accordance with claim 1 wherein $R_4$ is hydrogen.

10. The compound in accordance with claim 1 having the name 3a,4,13,13a-tetrahydro-2-methyl-4,13-ethano-1H,6H-pyrrolo[3',4':4,5]pyrido[1,2-c][1,3,5]benzoxadiazepine-1,3(2H)-dione.

* * * * *

UNITED STATES PATENT OFFICE
CERTIFICATE OF CORRECTION

Patent No. 4,022,790          Dated May 10, 1977

Inventor(s) Harry L. Yale et al.

It is certified that error appears in the above-identified patent and that said Letters Patent are hereby corrected as shown below:

Column 3, line 11, "4,13-ethano" should read --4,13-etheno--.

Column 4, line 8, "4,13-ethano" should read --4,13-etheno--.

Column 4, line 24, "1,3-" should read --1,3(2H)- --.

Example 10, Column II-first line, "-da,4,13,-" should read --3a,4,13,- --.

Example 13, Column II-second line should read: --hydro-4,13-ethano-1H,6H-pyrrolo(3',4':4,5]- --.

Example 15, Column II-second line, "pyrido 8 2-" should read --pyrido[2- --.

Example 18, Column II-third line, "ethao" should read --ethano--.

Example 19, Column II-third line, "[2,1-]" should read --[2,1-b]--.

Example 25, Column II-second line, "4,13-ethao" should read --4,13-ethano--.

Example 27, Column II-second line, "4,13-ethazo" should read --4,13-ethano--.

UNITED STATES PATENT OFFICE
CERTIFICATE OF CORRECTION

Patent No. 4,022,790　　　　　　　　Dated May 10, 1977

Inventor(s) Harry L. Yale et al.

It is certified that error appears in the above-identified patent and that said Letters Patent are hereby corrected as shown below:

Example 27, Column II-third line, "pyrido 8 1,2-c]" should read --pyrido[1,2-c]--.

Example 29, Column I-third line, "benzoxaidazepine" should read --benzoxadiazepine--.

Signed and Sealed this

First Day of November 1977

[SEAL]

Attest:

RUTH C. MASON　　　　　　　LUTRELLE F. PARKER
Attesting Officer　　　　Acting Commissioner of Patents and Trademarks